United States Patent [19]

Ruuskanen et al.

[11] Patent Number: 4,689,558

[45] Date of Patent: Aug. 25, 1987

[54] NON-DESTRUCTIVE METHOD OF MEASURING THE FATIGUE LIMIT OF FERROMAGNETIC MATERIALS BY USE OF THE MECHANICAL BARKHAUSER PHENOMENON

[76] Inventors: Pekka Ruuskanen, Makasiinik.16 A, 33230 Tampere 23, Finland; Pentti Kettunen, Liutuntie 15 D21, 33750 Tampere 75, Finland

[21] Appl. No.: 516,601

[22] PCT Filed: Nov. 18, 1981

[86] PCT No.: PCT/FI81/00086

§ 371 Date: Jun. 23, 1983

§ 102(e) Date: Jun. 23, 1983

[87] PCT Pub. No.: WO83/01836

PCT Pub. Date: May 26, 1983

[30] Foreign Application Priority Data

[FI] Finland ..............................................

[51] Int. Cl.⁴ ..................... G01B 7/24; G01N 29/04
[52] U.S. Cl. ................... 324/209; 324/262; 73/801
[58] Field of Search ............ 324/209, 262, 228; 73/779, 801, 587

[56] References Cited

U.S. PATENT DOCUMENTS 3,427,872  2/1969  Leep et al. ........................... 324/209

OTHER PUBLICATIONS

Karjalainen et al., "Detection of Plastic Deformation during Fatigue of Mild Steel by Measurement of Barkhausen Noise" NTD International Apr. 1979, pp. 51–55.

Karjalainen et al., "Detection of Plastic Deformation . . . ", NDT International, Apr. 1979, pp. 51–55.
Ketteinen et al., "The Influence of Cylic Stressing . . . " Scand. J. Metallurgy 8, Apr. 1979, pp. 112–114.

Primary Examiner—Reinhard J. Eisenzopf
Assistant Examiner—Walter E. Snow
Attorney, Agent, or Firm—Pollock, Vande Sande & Priddy

[57] ABSTRACT

A non-destructive method for using the mechanical Barkhausen noise phenomenon, caused in fereromagnetic materials by the dislocation motion and the changing external mechanical loading, especially in determining the fatigue strength of the material. The test piece is cyclically loaded with continuously or incrementally increasing amplitude in the presence or absence of a stable magnetic field by which the test piece is magnetized and, simultaneously, measurement is made of the maximum value obtained as a function of one of: the effective value, the size distribution and the mean value of the mechanical Barkhausen noise pulses induced during fatigue of the test piece. The loading amplitude at which such maximum value is reached corresponds to a fatigue strength equal to the fatigue limit of the test piece, the latter having been subjected to a prior loading process to create a lattice defect pattern in the test piece when no stable magnetizing field is present. The prior loading process comprises the steps of cyclically loading the test piece externally with continuously or incrementally increasing amplitude and simultaneously measuring the changes in the effective value, size distribution or mean value of the mechanical Barkhausen noise pulses induced during fatigue of the ferromagnetic test material caused by such loading and decreasing the external loading to zero.

13 Claims, 5 Drawing Figures

NON-DESTRUCTIVE METHOD OF MEASURING THE FATIGUE LIMIT OF FERROMAGNETIC MATERIALS BY USE OF THE MECHANICAL BARKHAUSER PHENOMENON

This invention relates to a measuring method used in the determination of the fatigue strength of ferromagnetic materials.

BACKGROUND OF THE INVENTION

Fatigue strength is presented by means of the so-called S-N curve which is experimentally determined by straining the test samples at different strain or stress amplitudes till the final fatigue fracture. One of the most important detail of the S-N curve is the endurance or fatigue limit, i.e. the limiting strain or stress amplitude under which the applied amplitudes are no longer capable of causing fatigue fracture or destruction of the samples. From this point of view of practical applications, the endurance or fatigue limit is also the most important value of the fatigue strength. Determination of this limit in the above mentioned destructive method requires a period of 5 to 10 days and nights depending on the testing machine used.

There exist also some non-destructive methods to measure fatigue tendency, mainly to follow the development of the structure deterioration associated with fatigue. A characteristic of these methods is that they require a comparison of the measured results with those of earlier measurements or those of reference materials. These methods, however, are proven to be rather unreliable, and, furthermore, with them one cannot measure the most important fatigue strength, the endurance of fatigue limit. Examples of these methods are, among others, the fatigue gauge method (fatigue wire methods) and measurements of the coersitive force.

The present non-destructive method of measuring the endurance or fatigue limit applies the so-called mechanical Barkhausen noise phenomenon. As a phenomenon, the mechanical Barkhausen noise formation is related to the irreversible changes in the magnetic state of the material (with the discontinuous movements of the domain walls under the influence of mechanical loading of the sample in a stable magnetic field or in a demagnetised state).

Better known is the "ordinary" Barkhausen noise effect which resulted from a changing external magnetic field. For the application of this "ordinary" Barkhausen noise effect in the non-destructive measuring technique a number of devices have been developed. For example the U.S. Pat. No. 3,427,872, teaching a method for the measurement of the static loading or strain state of a material by means of a changing external magnetic field is based on this "ordinary" noise effect. This method cannot be applied, however, to the analyzing of the mechanical Barkhausen noise, and may not be applied for the determination of the endurance or fatigue limit of the material.

The method of the present invention offers the notable advantage that the endurance or fatigue limit can, in practice, be determined very quickly, for example, in a period of 15 minutes. Therefore, the method of the present invention can in practice be applied to determine immediately whether the dynamic loading of a tested machine part is too large (above fatigue limit) or not.

The invention will now be described further by way of example only and with reference to the accompanying drawings.

DETAILED DESCRIPTION OF THE PREFERRED EMBODIMENTS

Figure 1:
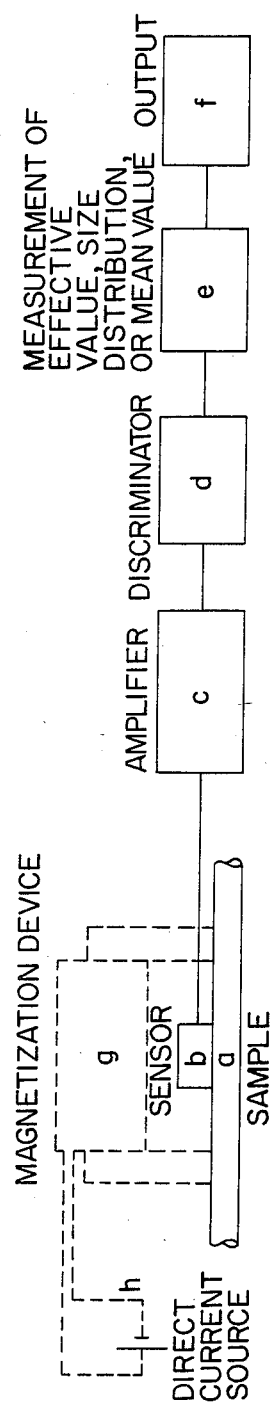
FIG. 1, shows a schematic view of the apparatus used to perform the method of the invention in a preferred embodiment thereof.

Referring to FIG. 1:
a. represents the sample under loading or straining
b. represents a sensor into which the mechanical Barkhausen phenomenon induces electromotoric force (voltage) pulses or signals; the sensor can be located away from the surface of the sample
c. represents an amplifier
d. represents a discriminator by which the wanted highest Barkhausen pulses are selected from the amplified noise signals for analysis
e. represents means for the measurement of size distribution, effective value, average of mean value, of frequency
f. represents an output device (print out or recording).

FIG. 1 represents by broken lines, and additionally by the letter g, the magnetization device by which the specimen or test piece can be magnetized with a stable magnetic field, the direction of which can be changed. The letter h shows additionally the direct current source associated with the magnetization device.

Figure 2A:
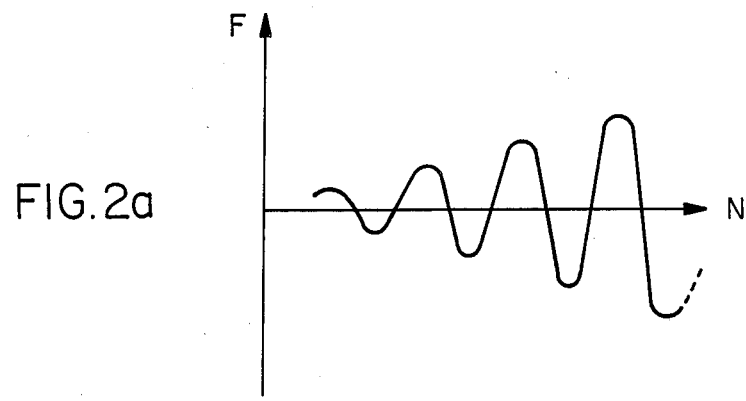
FIGS. 2a through 2d show graphical representations of measurement parameters of the method performed according to FIG. 1.
Figure 2B:
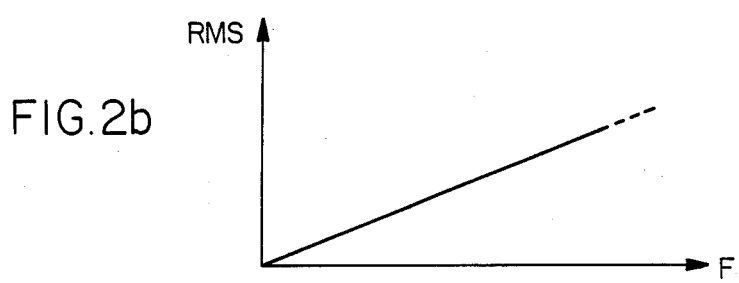

Measurement occurs in a number of stages stages as follows:

Stage 1: By means of an external cyclic loading a lattice defect arrangement is created in the test piece, which arrangement dominates the irreversible magnetization changes inside the test piece. For example, the mechanical loading amplitude F is increased, either continuously as shown in FIG. 2a or in steps, in which case each step is of the order of several amplitudes. Lattice defects, means, for example, dislocations, by means of which the plastic deformation of the material, and hence also the fatigue, occurs. As the loading amplitude is increased the effective value RMS of the mechanical Barkhausen noise pulses increases in correlation with the loading amplitude as shown in FIG. 2b.

Stage 2: The loading amplitude F is decreased to zero.

Figure 2C:
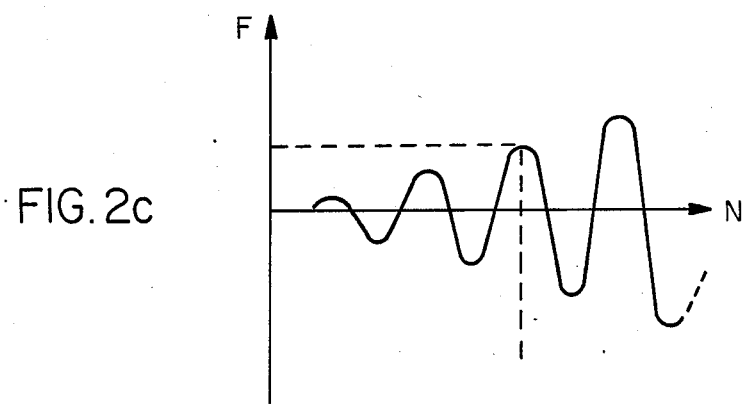
Figure 2D:
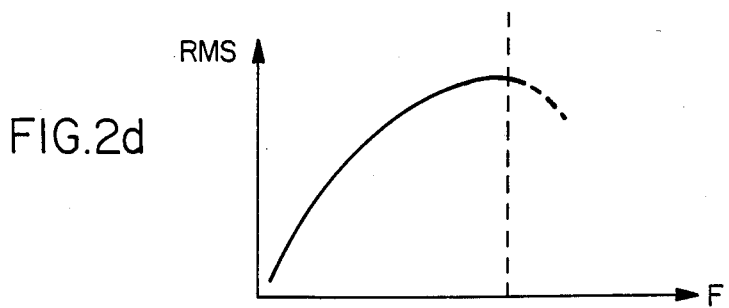

Stage 3: The loading amplitude F is increased again as shown in FIG. 2c. If the first increase of the loading amplitude F is carried to a sufficiently high value, the effective value RMS of the induced mechanical Barkhausen noise pulses goes through a maximum at a certain value of the loading amplitude F, as shown in FIG. 2d. This value of the loading amplitude is found to correspond very accurately to the endurance limit (or fatigue limit) of the original material.

It is not necessary to know beforehand the sufficiently high value of the loading amplitude into which the preliminary fatiguing is carried. It can be found experimentally by repeating stages 1 and 2 and at each repetition increasing the value of the maximum loading amplitude until the maximum point in the RMS-value according to stage 3 appears. Experiments have shown that the required maximum loading amplitude is about 60–70% of the tensile yield strength.

With the magnetization device g shown in FIG. 1 the test material can be magnetized with a stable magnetic field during measurement. Then the magnitude of the induced noise pulses increases and the changes at the endurance limit (fatigue limit) appear more clearly. By changing the direction of the magnetic field the magnetic state of the structure can additionally be influenced so that it becomes most effective in correlation to the direction of the acting load. For example, in iron-based metals the direction of the magnetic field must be parallel with that of the loading. It is also observed that the largest pulses of the mechanical Barkhausen noise are most sensitive against changes due to dislocations. when the largest pulses are selected for analysis by the discriminator d, the accuracy of the measured results increases.

The method can be applied by using a generally known apparatus.

Above, only two most beneficial application modes of the method of the present invention are presented. It is quite possible, for example, to measure changes in frequency, size distribution or mean value of the Barkhausen noise signals caused by dislocation motion instead of the above mentioned offective value RMS. Also the external loading, by which the maximum value of the Barkhausen noise of the present method is caused, can be other than a cyclic loading increasing in its amplitude. For example, repeated tension of compression can be used for this purpose.

The embodiments according to the method of the present invention can vary within the limits of the attached patent claims.

We claim:

1. A non-destructive method of measuring the fatigue limit of a ferro-magnetic test piece by use of the mechanical Barkhausen noise phenomenom which comprises:

cyclically loading said test piece externally with increasing amplitude and simultaneously measuring the maximum value obtained of a characteristic of the mechanical Barkhausen noise pulses induced during fatigue of said test piece, the loading amplitude at which said maximum value is reached corresponding to a fatigue strength equal to the fatigue limit of said test piece, said test piece having been subjected to a prior loading process to create a lattice defect pattern in the test piece, said prior loading process comprising the steps of cyclically loading said test piece externally with increasing amplitude, and simultaneously measuring the changes in a characteristic of the mechanical Barkhausen noise pulses induced during fatigue of the ferromagnetic test material caused by said loading; and decreasing the external loading to zero.

2. A method according to claim 1 wherein the amplitude of said cyclic loading increases continuously.

3. A method according to claim 1 wherein the amplitude of said cyclic loading increases incrementally.

4. A method according to claim 1 wherein said cyclically loading said test piece externally with incresing amplitude is performed in the presence of a stable magnetic field by which said test piece is magnetized.

5. A method according to claim 1 wherein said characteristic is the effective value of the mechanical Barkhausen noise pulses.

6. A method according to claim 1 wherein said characteristic is the size distribution of the mechanical Barkhausen noise pulses.

7. A method according to claim 1 wherein said characteristic is the mean value of the mechanical Barkhausen noise pulses.

8. A non-destructive method of measuring the fatigue limit of a ferromagnetic test piece by use of the mechanical Barkhausen noise phenomenom, which comprises:

(i) cyclically loading said test piece externally with increasing amplitude, and simultaneously measuring the changes in a characteristic of the mechanical Barkhausen noise pulses induced during fatigue of the ferromagnetic test material caused by said loading;

(ii) decreasing the external loading to zero; and (iii) cyclically loading said test piece externally with increasing amplitude and simultaneously measuring the maximum value obtained of a characteristic of the mechanical Barkhausen noise pulses induced during fatigue of said test piece, the loading amplitude at which said maximum value is reached corresponding to a fatigue strength equal to the fatigue limit of said test piece, the loading amplitude at which said maximum value is reached corresponding to a fatigue strength equal to the fatigue limit of said test piece.

9. A method according to claim 8 wherein the amplitude of said cyclic loading increases continuously.

10. A method according to claim 8 wherein the amplitude of said cyclic loading increases incrementally.

11. A method according to claim 8 wherein said characteristic is the effective value of the mechanical Barkhausen noise pulses.

12. A method according to claim 8 wherein said characteristic is the size distribution of the mechanical Barkhausen noise pulses.

13. A method according to claim 8 wherein said characteristic is the mean value of the mechanical Barkhausen noise pulses.

* * * * *